US012668773B2

(12) United States Patent
Shoji et al.

(10) Patent No.: US 12,668,773 B2
(45) Date of Patent: Jun. 30, 2026

(54) PRODUCTION METHOD FOR ORGANOID

(71) Applicants: JSR Corporation, Minato-ku (JP); KEIO UNIVERSITY, Minato-ku (JP)

(72) Inventors: Kentaro Shoji, Tokyo (JP); Toshiro Sato, Tokyo (JP)

(73) Assignees: JSR Corporation, Minato-ku (JP); KEIO UNIVERSITY, Minato-ku (JP)

( * ) Notice: Subject to any disclaimer, the term of this patent is extended or adjusted under 35 U.S.C. 154(b) by 1020 days.

(21) Appl. No.: 17/783,598

(22) PCT Filed: Dec. 15, 2020

(86) PCT No.: PCT/JP2020/046783
§ 371 (c)(1),
(2) Date: Jun. 8, 2022

(87) PCT Pub. No.: WO2021/125177
PCT Pub. Date: Jun. 24, 2021

(65) Prior Publication Data
US 2023/0002724 A1 Jan. 5, 2023

(30) Foreign Application Priority Data

Dec. 16, 2019 (JP) ................................. 2019-226710

(51) Int. Cl.
| | |
|---|---|
| *C12N 5/074* | (2010.01) |
| *C07K 14/47* | (2006.01) |
| *C07K 14/485* | (2006.01) |
| *C07K 14/50* | (2006.01) |
| *C12N 5/07* | (2010.01) |

(52) U.S. Cl.
CPC ............ *C12N 5/06* (2013.01); *C07K 14/4743* (2013.01); *C07K 14/485* (2013.01); *C07K 14/50* (2013.01)

(58) Field of Classification Search
None
See application file for complete search history.

(56) References Cited

U.S. PATENT DOCUMENTS

| | | | | | |
|---|---|---|---|---|---|
| 2010/0286042 | A1* | 11/2010 | Imamura | ................... | A61P 7/00 |
| | | | | | 514/9.1 |
| 2014/0256037 | A1* | 9/2014 | Sato | ......................... | A61P 1/04 |
| | | | | | 435/377 |

| | | | |
|---|---|---|---|
| 2015/0299280 | A1 | 10/2015 | Nakayama et al. |
| 2019/0390171 | A1 | 12/2019 | Sato et al. |
| 2020/0157507 | A1 | 5/2020 | Matsunaga et al. |

FOREIGN PATENT DOCUMENTS

| | | | |
|---|---|---|---|
| EP | 213 296 | A1 | 8/2010 |
| EP | 3 460 042 | A1 | 3/2019 |
| JP | 2014-100141 | A | 6/2014 |
| WO | WO 2009/048119 | A1 | 4/2009 |
| WO | WO 2017/199811 | A1 | 11/2017 |
| WO | WO 2018/207714 | A1 | 11/2018 |

OTHER PUBLICATIONS

International Search Report issued Mar. 2, 2021 in PCT/JP2020/046783 filed on Dec. 15, 2020, citing documents AA-AC, AP-AR and AY therein, 5 pages (with English Translation).
Huch, M. et al., "Long-Term Culture of Genome-Stable Bipotent Stem Cells from Adult Human Liver", Cell 160, pp. 299-312, 2015.
Huch, M. et al., "Modeling mouse and human development using organoid cultures", Development, vol. 142, pp. 3113-3125, doi:10.1242/dev.118570, 2015.
Extended European Search Report issued Jan. 12, 2024 in European Patent Application No. 20901631.0, citing references 1 and 15-16 therein, 9 pages.
Combined Chinese Office Action and Search Report issued Jul. 30, 2023, in corresponding Chinese Patent Application No. 202080085820.9 (with English Translation) citing document 24 therein, 17 pages.
Masayuki Fujii et al., "Human intestinal organoids maintain self-renewal capacity and cellular diversity in niche-inspired culture condition", Cell Stem Cell, vol. 23, 787-793, pp. e1-e6.

* cited by examiner

*Primary Examiner* — Maria G Leavitt
*Assistant Examiner* — Brendan Thomas Tinsley
(74) *Attorney, Agent, or Firm* — Oblon, McClelland, Maier & Neustadt, L.L.P.

(57) ABSTRACT

A production method for an organoid, the production method including a step of culturing adult stem cells or a cell tissue piece including adult stem cells in a medium containing a chimeric Fibroblast Growth Factor (FGF) that includes a partial region of FGF1 and a partial region of FGF2; an organoid produced by the production method; a medium including a chimeric FGF and having a content of chimeric FGF of 50 ng/mL or less; and an evaluation method for a test substance are provided, and according to the chimeric FGF, a content of growth factors included in a medium can be reduced.

13 Claims, 7 Drawing Sheets

Specification includes a Sequence Listing.

FGF2
(ng/mL)

10

5

2.5

FGF2
(ng/mL)

10

5

2.5

FGFC
(ng/mL)

10

5

2.5

FGFC
(ng/mL)

10

5

2.5

FGFC
(ng/mL)

10

5

2.5

FGFC-V
(ng/mL)

10

5

2.5

FGFC-I
(ng/mL)

10

5

2.5

FGFC-L
(ng/mL)

10

5

2.5

FGFC
(ng/mL)

50

12.5

3.1

FGFC-V
(ng/mL)

50

12.5

3.1

FGFC-I
(ng/mL)

50

12.5

3.1

FGFC-L
(ng/mL)

50

12.5

3.1

TEMPERATURE(°C)

SEQUENCE LISTING

<160> NUMBER OF SEQ ID NOS: 4

<210> SEQ ID NO 1
<211> LENGTH: 136
<212> TYPE: PRT
<213> ORGANISM: Artificial Sequence
<220> FEATURE:
<223> OTHER INFORMATION: Synthesized peptide named FGFC and derived from
      human FGF1 and human FGF2

<400> SEQUENCE: 1

Met Ala Asn Tyr Lys Lys Pro Lys Leu Leu Tyr Cys Ser Asn Gly Gly
1               5                   10                  15

His Phe Leu Arg Ile His Pro Asp Gly Arg Val Asp Gly Val Arg Glu
            20                  25                  30

Lys Ser Asp Pro His Ile Lys Leu Gln Leu Gln Ala Glu Glu Arg Gly
        35                  40                  45

Val Val Ser Ile Lys Gly Val Cys Ala Asn Arg Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe
        115                 120                 125

Leu Pro Leu Pro Val Ser Ser Asp
    130                 135

<210> SEQ ID NO 2
<211> LENGTH: 136
<212> TYPE: PRT
<213> ORGANISM: Artificial Sequence
<220> FEATURE:
<223> OTHER INFORMATION: Synthesized peptide named FGFC-V and derived
      from human FGF1 and human FGF2

<400> SEQUENCE: 2

Met Ala Asn Tyr Lys Lys Pro Lys Leu Leu Tyr Cys Ser Asn Gly Gly
1               5                   10                  15

His Phe Leu Arg Ile His Pro Asp Gly Arg Val Asp Gly Val Arg Glu
            20                  25                  30

Lys Ser Asp Pro His Ile Lys Leu Gln Leu Val Ala Glu Glu Arg Gly
        35                  40                  45

Val Val Ser Ile Lys Gly Val Cys Ala Asn Arg Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe
        115                 120                 125

Leu Pro Leu Pro Val Ser Ser Asp
    130                 135

-continued

<210> SEQ ID NO 3
<211> LENGTH: 136
<212> TYPE: PRT
<213> ORGANISM: Artificial Sequence
<220> FEATURE:
<223> OTHER INFORMATION: Synthesized peptide named FGFC-I and derived
      from human FGF1 and human FGF2

<400> SEQUENCE: 3

Met Ala Asn Tyr Lys Lys Pro Lys Leu Leu Tyr Cys Ser Asn Gly Gly
1               5                   10                  15

His Phe Leu Arg Ile His Pro Asp Gly Arg Val Asp Gly Val Arg Glu
            20                  25                  30

Lys Ser Asp Pro His Ile Lys Leu Gln Leu Ile Ala Glu Glu Arg Gly
        35                  40                  45

Val Val Ser Ile Lys Gly Val Cys Ala Asn Arg Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe
        115                 120                 125

Leu Pro Leu Pro Val Ser Ser Asp
    130                 135

<210> SEQ ID NO 4
<211> LENGTH: 136
<212> TYPE: PRT
<213> ORGANISM: Artificial Sequence
<220> FEATURE:
<223> OTHER INFORMATION: Synthesized peptide named FGFC-L and derived
      from human FGF1 and human FGF2

<400> SEQUENCE: 4

Met Ala Asn Tyr Lys Lys Pro Lys Leu Leu Tyr Cys Ser Asn Gly Gly
1               5                   10                  15

His Phe Leu Arg Ile His Pro Asp Gly Arg Val Asp Gly Val Arg Glu
            20                  25                  30

Lys Ser Asp Pro His Ile Lys Leu Gln Leu Leu Ala Glu Glu Arg Gly
        35                  40                  45

Val Val Ser Ile Lys Gly Val Cys Ala Asn Arg Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe
        115                 120                 125

Leu Pro Leu Pro Val Ser Ser Asp
    130                 135

PRODUCTION METHOD FOR ORGANOID

TECHNICAL FIELD

The present invention relates to a production method for an organoid. More particularly, the present invention relates to a production method for an organoid, a medium, an organoid, an evaluation method for a test substance, and a chimeric FGF. Priority is claimed on Japanese Patent Application No. 2019-226710, filed Dec. 16, 2019, the content of which is incorporated herein by reference.

BACKGROUND ART

An organoid is a mass of cultured cells formed as cells accumulate, and has a structure and functions similar to those of an organ in a living body. In recent years, studies have been actively conducted to produce various organoids from stem cells such as somatic stem cells, embryonic stem cells (ES cells), and artificial pluripotent stem cells (iPS cells), and for example, brain organoids, intestinal organoids, liver organoids, kidney organoids, gastric organoids, lung organoids, ovarian cancer organoids, and biliary tract cancer organoids have been produced.

The production of organoids from stem cells has been carried out by controlling signaling pathways and inducing proliferation, differentiation, and the like of stem cells. The MAPK signaling pathway is known to be a signaling pathway that controls proliferation, growth, differentiation, and transformation of stem cells, apoptosis, and the like. Furthermore, it is known that the MAPK signaling pathway is down-regulated by growth factors such as basic fibroblast growth factor (Fibroblast Growth Factor 2, FGF2) and epidermal growth factor (Epidermal Growth Factor, EGF). These growth factors are components that are usually added to a medium for producing organoids from stem cells (see Patent Document 1 and Non-Patent Document 1).

CITATION LIST

Patent Document

[Patent Document 1]
European Patent Application, Publication No. 3460042

Non-Patent Document

[Non-Patent Document 1]
Huch M., et al., Long-term culture of genome-stable bipotent stem cells from adult human liver, Cell, 160 (1-2), 299-312, 2015.

SUMMARY OF INVENTION

Technical Problem

However, in the production of organoids from stem cells, it is necessary to exchange the medium regularly during cell culture because the medium components become inactivated. Particularly, when organoids are used for regenerative medicine, drug screening, and the like, organoids of sufficient sizes are required, and the number of times the medium needs to be exchanged also increases accordingly. On the other hand, growth factors such as FGF2 and EGF are very expensive and have a risk of containing endotoxin and the like. Therefore, it is desirable to reduce the amount of growth factors that are added to the medium. Thus, an object of the present invention is to provide a technology for producing organoids by which the content of the growth factors to be included in a medium can be reduced.

Solution to Problem

The present invention includes the following embodiments.

[1] A production method for an organoid, the production method including:
a step of culturing adult stem cells or a cell tissue piece including adult stem cells in a medium containing a chimeric Fibroblast Growth Factor (FGF) that includes a partial region of FGF 1 and a partial region of FGF2.

[2] The production method according to [1],
in which a content of the chimeric FGF included in the medium is 50 ng/mL or less.

[3] The production method according to [1] or [2],
in which the medium further contains Epidermal Growth Factor (EGF).

[4] The production method according to [3],
in which a total content of the chimeric FGF and the EGF included in the medium is 100 ng/mL or less.

[5] The production method according to any one of [1] to [4],
in which the chimeric FGF is a protein having an amino acid sequence set forth in any one of SEQ ID NO:1 to SEQ ID NO:4, or a protein having an amino acid sequence in which one or several amino acids are deleted, substituted, or added with respect to an amino acid sequence set forth in any one of SEQ ID NO:1 to SEQ ID NO:4, and having an activity capable of producing an organoid from adult stem cells or a cell tissue piece including adult stem cells by incorporating 50 ng/mL or less of the protein into a medium.

[6] The production method according to any one of [1] to [5],
in which the medium further contains an Insulin-like growth factor (IGF) signaling pathway promoter.

[7] The production method according to any one of [1] to [6],
in which the medium further contains a Transforming Growth Factor-β (TGF-β) signaling pathway inhibitor.

[8] The production method according to any one of [1] to [7],
in which the medium further contains a Wnt signaling pathway promoter.

[9] The production method according to any one of [1] to [8],
in which the medium further contains a Rho-kinase (ROCK) signaling pathway inhibitor.

[10] The production method according to any one of [1] to [9],
in which the medium further contains a Bone morphogenetic protein (BMP) signaling pathway inhibitor.

[11] A medium including a chimeric FGF,
in which a content of the chimeric FGF is 50 ng/mL or less.

[12] The medium according to Claim 11,
in which the medium further includes EGF, and a total content of the chimeric FGF and the EGF is 100 ng/mL or less.

[13] An organoid produced by the method according to any one of [1] to [10].

[14] An evaluation method for a test substance, the method including:
a step of bringing the organoid according to [13] into contact with a test substance; and

a step of evaluating an influence exerted by the test substance on the organoid.

[15] A chimeric EGF, which is a protein having an amino acid sequence set forth in any one of SEQ ID NO:1 to SEQ ID NO:4, or a protein having an amino acid sequence in which one or several amino acids are deleted, substituted, or added with respect to an amino acid sequence set forth in any one of SEQ ID NO:1 to SEQ ID NO:4, and having an activity capable of producing an organoid from adult stem cells or a cell tissue piece including adult stem cells by incorporating 50 ng/mL or less of the protein into a medium.

Advantageous Effects of Invention

According to the present embodiment, an organoid production technology capable of reducing the content of growth factors included in the medium can be provided.

BRIEF DESCRIPTION OF DRAWINGS

FIG. 3I is a micrograph of organoids formed in Experimental Example 3.

4

Figures 6A, 6B, 6C, 6D:
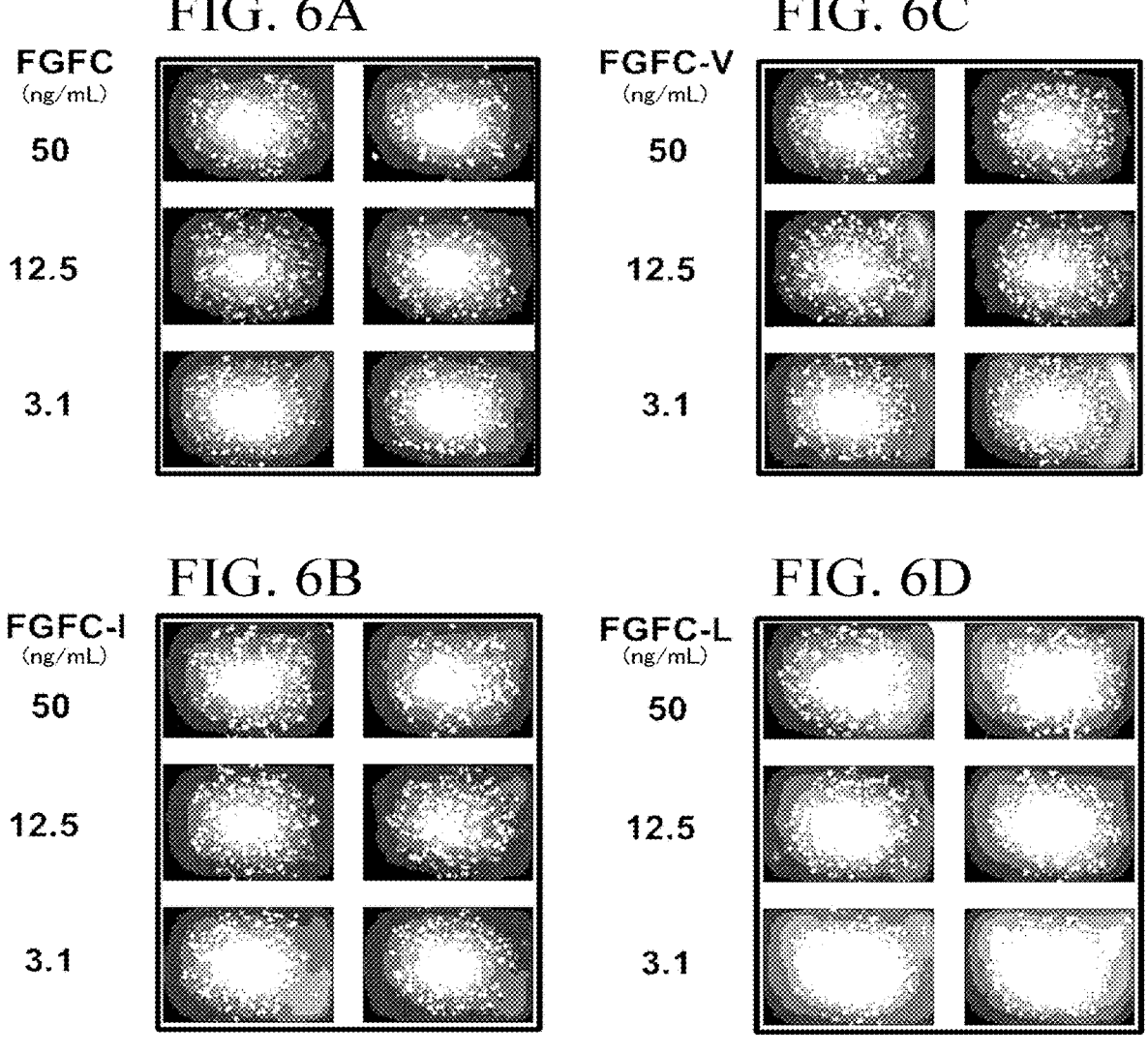
FIG. 6A is a micrograph of organoids formed in Experimental Example 3.
FIG. 6B is a micrograph of organoids formed in Experimental Example 3.
FIG. 6C is a micrograph of organoids formed in Experimental Example 3.

FIG. 6D is a micrograph of organoids formed in Experimental Example 3.

Figure 7:
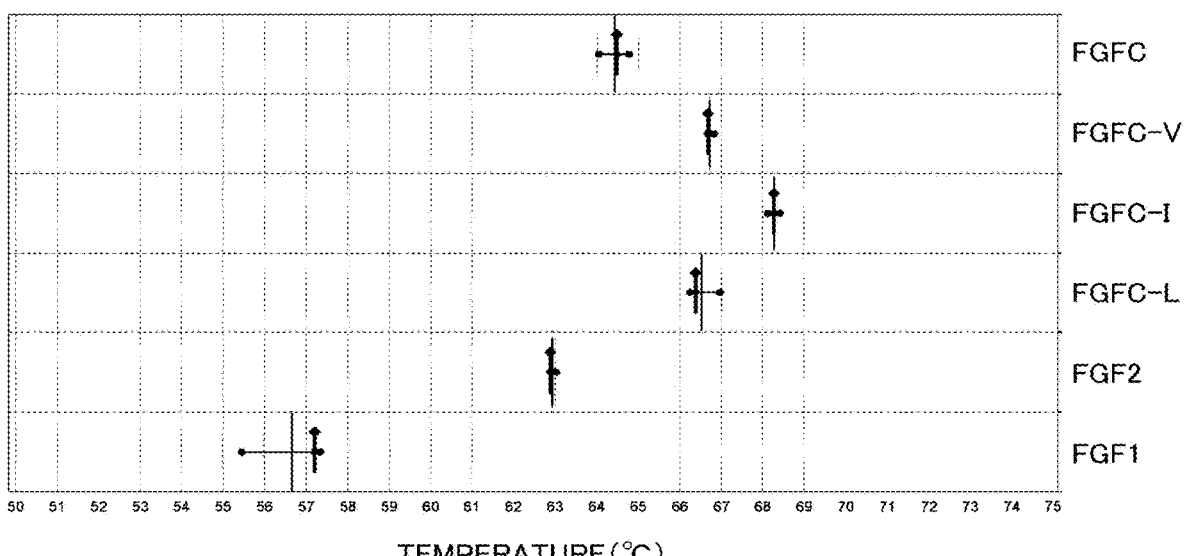

FIG. 7 is a graph showing the melting temperature (Tm) of an FGFC mutant measured in Experimental Example 4.

DESCRIPTION OF EMBODIMENTS

Hereinafter, the present invention will be described in more detail by way of embodiments; however, the present invention is not intended to be limited to the following embodiments.

Unless stated otherwise, regarding each component mentioned as an exemplary example in the present specification, for example, a component included in a medium or a component used in each step, one kind thereof may be used alone, or two or more kinds thereof may be used in combination.

In the present specification, the notation representing a numerical value range such as "A to B" is synonymous with "A or greater and B or less" and implies that A and B are included in the numerical value range.

In the present specification, the terms "medium including substance X" and "in the presence of substance X" mean a medium to which an exogenous substance X has been added, a medium including an exogenous substance X, or in the presence of an exogenous substance X. That is, when a cell or tissue present in the medium expresses, secretes, or produces the substance X endogenously, the endogenous substance X is distinguished from the exogenous substance X, and it is to be noted that a medium which does not include the exogenous substance X does not fall under the category of "medium including substance X" even when the medium includes the endogenous substance X.

[Production Method for Organoid]

One embodiment is a production method for an organoid, the production method including: a step of culturing adult stem cells or a cell tissue piece including adult stem cells in a medium containing a chimeric FGF (hereinafter, also referred to as "FGFC") that includes a partial region of Fibroblast growth factor (FGF) 1 and a partial region of FGF2.

According to the production method of the present embodiment, the content of growth factors to be added to the medium in the production of an organoid can be reduced. The production method of the present embodiment is particularly suitable for producing organoids such as intestinal organoids, liver organoids, ovarian cancer organoids, lung organoids, and gastric organoids.

With regard to the production of an organoid, the reason why the content of growth factors included in a medium could be reduced by incorporating a chimeric FGF in the medium is presumed to be as follows. That is, it is known that FGF has a fixed fibroblast growth factor receptor (FGFR) that reacts with FGF, and there are seven types including isoforms. It is speculated that by chimerizing FGF, the chimeric forms are enabled to react with many types of FGFR, and as a result, cells could be cultured even at a low concentration. Particularly, epithelial stem cells, which are important for culturing adult stem cells, are said to highly express FGFR2b; however, FGF2 does not have good reactivity with FGFR2b. On the other hand, it is known that FGF1 can react with all seven types of FGFR including FGFR2b, and it is speculated that FGFC having the properties of both FGF2 and FGF1 can react with FGFR2b, and as a result, the cells could be cultured even at a low concentration.

Adult stem cells are stem cells which are also called somatic stem cells, tissue stem cells, and cancer stem cells, and are cells that are present in the body of a living body and have not undergone terminal differentiation. Adult stem cells usually have an ability to differentiate into a plurality of specific kinds of cells. In the production method of the present embodiment, the adult stem cells may be cells maintained in culture or may be primary cells present in a tissue extracted from an adult organism. Furthermore, epithelial stem cells are preferred as the adult stem cells.

In the present specification, cell aggregates are referred to as cell masses. Furthermore, among cell masses, in particular, a cell mass that includes adult stem cells and cells differentiated from adult stem cells and has a structure and functions similar to those of an organ in a living body is referred to as an organoid.

In the production method of the present embodiment, as the medium, a medium obtained by adding a chimeric FGF to a basal medium can be used. Examples of the basal medium include BME medium, BGJb medium, CMRL 1066 medium, Glasgow's MEM (GMEM) medium, Improved MEM Zinc Option medium, IMDM medium, Medium 199 medium, Eagle's MEM medium, aMFM medium, DMEM medium, F-12 medium. DMEM/F12 medium. IMDM/F12 medium. Ham's medium, RPMI 1640 medium, and Fischer's medium. As the basal medium, a medium in which these media are mixed may also be used.

The chimeric FGF according to the production method of the present embodiment is a fusion protein including a partial region of FGF1 and a partial region of FGF2. Examples of the NCBI accession number of human FGF1 protein include NP_001244138.1, NP_001244137.1, and NP_001341881.1. Examples of the NCBI accession number of mouse FGF1 protein include NP 034327.1. Examples of the NCBI accession number of human FGF2 protein include NP_001348594.1 and NP_001997.5. Examples of the NCBI accession number of mouse FGF2 protein include NP_032032.1.

As the chimeric FGF, a protein having an amino acid sequence set forth in any one of SEQ ID NO:1 to SEQ ID NO:4 is preferred. The chimeric FGF may have a mutation with respect to a protein having the amino acid sequence set forth in any one of SEQ ID NO:1 to SEQ ID NO:4, as long as the mutated chimeric FGF has an activity capable of producing an organoid from adult stem cells or a cell tissue piece including adult stem cells by incorporating 50 ng/mL or less of the mutated chimeric FGF into the medium.

That is, the chimeric FGF may be a protein having an amino acid sequence in which one or several amino acids are deleted, substituted, or added with respect to the amino acid sequence set forth in any one of SEQ ID NO:1 to SEQ ID NO:4. Here, one or several means 1 to 10, preferably 1 to 5, more preferably 1 to 3, and even more preferably 1 to 2.

With regard to the amino acid sequence of the chimeric FGF, it is preferable that the amino acid corresponding to the 43rd amino acid in the amino acid sequence of SEQ ID NO:1 be glutamine, valine, isoleucine, or leucine.

A chimeric FGF in which the amino acid corresponding to the 43rd amino acid in the amino acid sequence of SEQ ID NO:1 is glutamine, valine, isoleucine, or leucine has high heat resistance compared with FGF1 and FGF2 and is stable.

Above all, the chimeric FGF in which the amino acid corresponding to the 43rd amino acid in the amino acid sequence of SEQ ID NO:1 is isoleucine has a particularly high melting temperature (Tm) and has high heat resistance.

The amino acid corresponding to the 43rd amino acid in the amino acid sequence of SEQ ID NO:1 can be specified by, for example, aligning a target amino acid sequence with the amino acid sequence of SEQ ID NO:1 by using an alignment program such as ClustalW.

In the past, in the production of organoids, it has been conventional to add about 100 ng/mL of FGF2 into the medium. In contrast, the content of the chimeric FGF included in the medium can be reduced by using a chimeric FGF instead of FGF2. The content of the chimeric FGF included in the medium is usually 50 ng/mL or less, preferably 20 ng/mL or less, more preferably 15 ng/mL or less, even more preferably 10 ng/mL or less, and particularly preferably 5 ng/mL or less.

In the production method of the present embodiment, the medium may further contain Epidermal Growth Factor (EGF). When the medium includes EGF, the total content of the chimeric FGF and EGF included in the medium can be reduced. When the medium includes EGF, the total content of the chimeric FGF and EGF included in the medium is usually 100 ng/mL or less, and preferably 70 ng/mL or less.

The NCBI accession number of human EGF protein is NP_001171601.1.

With regard to the production method of the present embodiment, it is preferable that the medium further contain a Wnt signaling pathway promoter.

Examples of the Wnt signaling pathway promoter include a Wnt family member, R-spondin, norrin, and a GSK-3p inhibitor. Among these, a Wnt family member and R-spondin are preferred.

Examples of the Wnt family members include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

As the Wnt family member, Wnt3a or Wnt4 is preferred, and Wnt3a is more preferred. Wnt3a is preferably a complex with Afamin in order to enhance stability.

When Wnt3a is used as a Wnt signaling pathway promoter, the concentration of Wnt3a included in the medium is usually 10 ng/mL to 10 μg/mL, preferably 10 ng/mL to 1 μg/mL, and for example, 100 ng/mL to 700 ng/mL.

Examples of R-spondin include R-spondin 1, R-spondin 2, R-spondin 3, and R-spondin 4.

Examples of the NCBI accession number of human R-spondin 1 protein include NP_001229838.1 and XP_006710646.1. Examples of the NCBI accession number of mouse R-spondin 1 protein include NP_619624.2. Examples of the NCBI accession number of human R-spondin 2 protein include XP_011515320.1, XP_011515321.1, and NP_848660.3. Examples of the NCBI accession number of mouse R-spondin 2 protein include NP_766403.1. Examples of the NCBI accession number of human R-spondin 3 protein include XP_016866867.1, XP_016866868.1, and NP_116173.2. Examples of the NCBI accession number of mouse R-spondin 3 protein include NP_082627.3. Examples of the NCBI accession number of human R-spondin 4 protein include NP_001035096.1 and NP_001025042.2. Examples of the NCBI accession number of mouse R-spondin 4 protein include NP_001035779.1.

When R-spondin is used as a Wnt signaling pathway promoter, the concentration of R-spondin included in the medium is usually 10 ng/mL to 10 μg/mL, preferably 10 ng/mL to 1 μg/mL, more preferably 100 ng/mL to 500 ng/mL.

Examples of the GSK-3β inhibitor include CHIR99021 (CAS number: 252917-06-9), Kenpaullone (CAS number: 142273-20-9), and 6-Bromoindirubin-3'-oxime (BIO, CAS number: 667463-62-9).

When a GSK-3β inhibitor is used as a Wnt signaling pathway promoter, the concentration of the GSK-3β inhibitor included in the medium is usually 0.1 µM to 10 µM.

With regard to the production method of the present embodiment, it is preferable that the medium further contain an Insulin-like growth factor (IGF) signaling pathway promoter.

Examples of the IGF signaling pathway promoter include IGF-1 and IGF-2, and IGF-1 is preferred. Examples of the NCBI accession number of human IGF-1 protein include NP_001104753.1 and NP_001104755.1. Examples of the NCBI accession number of mouse IGF-1 protein include NP_001104745.1. Examples of the NCBI accession number of human IGF-2 protein include NP_001007140.2 and NP_001278790.1. Examples of the NCBI accession number of mouse IGF-2 protein include NP_034644.2 and NP_001302418.1.

In the production method of the present embodiment, it is preferable that the medium further contain a Transforming Growth Factor-β (TGF-β) signaling pathway inhibitor.

A TGF-β signaling pathway inhibitor is a substance that inhibits the signaling pathways transduced by the Smad family. Examples of the TGF-β signaling pathway inhibitor include A83-01 (CAS number: 909910-43-6), SB-431542 (CAS number: 301836-41-9), SB-505124 (CAS number: 694433-59-5), SB-525334 (CAS number: 356559-20-1). LY364947 (CAS number: 396129-53-6), SC-203294 (CAS number: 627536-09-08). SD-208 (CAS number: 627536-09-8), and SJN2511 (CAS number: 446859-33-2). Among these, A83-01 and SB-431542 are preferred.

The concentration of the TGF-β signaling pathway inhibitor included in the medium is usually 10 nM to 100 µM, and preferably 100 nM to 10 µM.

In the production method of the present embodiment, it is preferable that the medium further contain a Rho-kinase (ROCK) signaling pathway inhibitor.

Examples of the ROCK signaling pathway inhibitor include Y-27632 (CAS number: 129830-38-2), Fasudil/HA1077 (CAS number: 105628-07-7), H-1152 (CAS number: 871543-07-6). Wf-536 (CAS number: 539857-64-2), and derivatives thereof.

The concentration of the ROCK signaling pathway inhibitor included in the medium is usually 0.1 µM to 100 µM, preferably 0.1 µM to 50 µM, and more preferably 0.1 µM to 30 µM.

In the production method of the present embodiment, it is preferable that the medium further contain a Bone morphogenetic protein (BMP) signaling pathway inhibitor.

Examples of the BMP signaling pathway inhibitor include Noggin, chordin, follistatin, dorsomorphin (CAS number: 866405-64-3), DMH1 (CAS number: 1206711-16-1), and LDN193189 (CAS number: 1062368-24-4).

The concentration of the BMP signaling pathway inhibitor included in the medium is usually 0.5 µM to 10 µM. When Noggin is used as the BMP signaling pathway inhibitor, the concentration of Noggin included in the medium is usually 10 ng/mL to 1000 ng/mL, preferably 10 ng/mL to 500 ng/mL, and more preferably 10 ng/mL to 300 ng/mL.

In the production method of the present embodiment, the medium may further contain a medium supplement, an antibacterial agent, blood serum, a serum substitute, insulin, albumin, and the like as other additives.

Examples of the medium supplement include a supplement for culturing nerve cells, such as product name "B-27 serum-free supplement" (Thermo Fisher Scientific, Inc.); a glutamine-containing supplement containing L-glutamine, L-alanyl-L-glutamine, and the like, such as product name "GlutaMax" (Thermo Fisher Scientific, Inc.); an aqueous solution of amino acids, such as "MEM Non-Essential Amino Acids Solution" (Thermo Fisher Scientific, Inc.); and 2-mercaptoethanol.

Examples of the antibacterial agent include a penicillin-based antibiotic substance, a cephem-based antibiotic substance, a macrolide-based antibiotic substance, a tetracycline-based antibiotic substance, a fosfomycin-based antibiotic substance, an aminoglycoside-based antibiotic substance, and a new quinolone-based antibiotic substance.

When culturing adult stem cells or a cell tissue piece including adult stem cells, the cells may be embedded in an extracellular matrix (ECM), or ECM may be added to the medium. Examples of the ECM include components included in the basement membrane and glycoproteins present in the intercellular spaces. Examples of the components included in the basement membrane include type IV collagen, laminin, heparan sulfate proteoglycan, and entactin. Examples of the glycoprotein present in the intercellular space include collagen, laminin, entactin, fibronectin, and heparin sulfate. Regarding the ECM, a commercially available product including the ECM may be used. Examples of a commercially available product including ECM include Matrigel (registered trademark, Corning, Inc.) and human laminin (Sigma-Aldrich Corporation).

Matrigel contains basement membrane components derived from Engelbreth Holm Swarm mouse sarcoma. Main components of Matrigel include type IV collagen, laminin, heparan sulfate proteoglycan, and entactin; however, in addition to these, various growth factors such as epidermal growth factor (EGF), nerve growth factor (NGF), platelet-derived growth factor (PDGF), insulin-like growth factor 1 (IGF-1), and TGF-β are included. Matrigel is also available in grades with low concentrations of various growth factors, and the concentrations of the growth factors are less than 0.5 ng/mL for EGF, less than 0.2 ng/mL for NGF, less than 5 µg/mL for PDGF, less than 5 ng/mL for IGF-1, and less than 1.7 ng/mL for TGF-β. Regarding Matrigel, it is preferable to use a grade having a low content ratio of various growth factors.

When culturing adult stem cells or a cell tissue piece including adult stem cells, it is preferable to exchange the medium about once every 1 to 5 days. When the formed organoid is large, it is preferable to disperse the organoid. Dispersing means that cells are separated into cell populations of 10,000 or fewer cells by a dispersing treatment such as an enzyme treatment or a physical treatment. Dispersing can be performed by treating the organoid with a cell dispersion liquid, or the like.

Examples of the cell dispersion liquid include solutions including enzymes such as trypsin, collagenase, hyaluronidase, elastase, pronase, DNase, and papain; or a chelating agent such as ethylenediaminetetraacetic acid. A commercially available cell dispersion liquid can also be used as the cell dispersion liquid. Examples of a commercially available cell dispersion liquid include TrypLE Select and TrypLE Express manufactured by Thermo Fisher Scientific, Inc.

[Medium]

One embodiment is a medium including a chimeric FGF, in which a content of the chimeric FGF is 50 ng/mL or less. An organoid can be produced by culturing adult stem cells or a cell tissue piece including adult stem cells in the medium of the present embodiment. Therefore, the medium of the present embodiment can be said to be a medium for organoid production.

The medium of the present embodiment is a basal medium to which a chimeric FGF has been added. The basal medium and the chimeric FGF are similar to those described above.

The medium of the present embodiment preferably further includes EGF, and the total content of the chimeric FGF and the EGF is 100 ng/mL or less. The EGF is the same as described above.

The medium of the present embodiment can further contain a Wnt signaling pathway promoter, an IGF signaling pathway promoter, a TGF-β signaling pathway inhibitor, a ROCK signaling pathway inhibitor, a BMP signaling pathway inhibitor, and other additives. Each of these components is the same as described above.

[Organoid]

One embodiment is an organoid produced by the above-mentioned production method. Since the organoid of the present embodiment can be produced at a reduced cost required for growth factors and the like, it is easy to produce the organoid in large quantities at low cost. Therefore, for example, the organoid can be suitably used for use applications where an evaluation of a test substance and the like, which will be described later, is carried out in a large scale.

The organoid of the present embodiment is produced by using a chimeric FGF instead of FGF2 that has been conventionally used. Therefore, there is a possibility that there may be a difference in the gene expression profile and the like between the organoid of the present embodiment and the organoid produced by the conventional production method. However, since enormous trial and error and efforts are required to identify such a difference, it is considered that it is not realistic to specify the organoid of the present embodiment by a gene expression profile or the like, and it is realistic to specify the organoid by the production method.

[Evaluation Method for Test Substance]

One embodiment is an evaluation method for a test substance, the method including a step of bringing an organoid produced by the above-mentioned production method into contact with a test substance; and a step of evaluating the influence exerted by the test substance on the organoid.

By the method of the present embodiment, an evaluation of a test substance can be carried out by using an organoid having a structure and functions similar to those of cells in vivo. The method of the present embodiment can be applied to screening of therapeutic agents for various diseases, and the like.

Examples of the test substance include a natural compound library, a synthetic compound library, an existing drug library, and a metabolite library.

The influence exerted by the test substance on the organoid can be evaluated at, for example, the gene level, the protein level, and the metabolite level. The influence exerted by the test substance on the organoid can be evaluated by evaluating the morphology of the organoid.

Evaluation at the gene level can be performed by, for example, an RNA-seq analysis, a DNA microarray analysis, or a real-time PCR. Furthermore, evaluation at the protein level can be performed by, for example, Western blotting, ELISA, or immunostaining. Furthermore, evaluation at the metabolite level can be evaluated by, for example, liquid chromatography (LC), mass spectrometry (MS), or LC/MS. Furthermore, evaluation of the morphology of an organoid can be performed by, for example, microscopic observation or immunostaining.

[Chimeric FGF]

One embodiment is a chimeric FGF, which is a protein having an amino acid sequence set forth in any one of SEQ ID NO:1 to SEQ ID NO:4, or a protein having an amino acid sequence in which one or several amino acids are deleted, substituted, or added with respect to an amino acid sequence set forth in any one of SEQ ID NO:1 to SEQ ID NO:4, and having an activity capable of producing an organoid from adult stem cells or a cell tissue piece including adult stem cells by incorporating 50 ng/mL or less of the protein into a medium.

As will be described later in the Examples, by using the chimeric FGF of the present embodiment, the content of growth factors to be added to the medium can be reduced in the production of an organoid.

Furthermore, as described above, with regard to the amino acid sequence of the chimeric FGF, it is preferable that the amino acid corresponding to the 43rd amino acid in the amino acid sequence of SEQ ID NO:1 be glutamine, valine, isoleucine, or leucine.

Above all, from the viewpoint of having high heat resistance and being stable, the amino acid corresponding to the 43rd amino acid in the amino acid sequence of SEQ ID NO:1 is preferably valine, isoleucine, or leucine, and more preferably isoleucine.

EXAMPLES

Hereinafter, the present embodiment will be described in more detail based on Examples; however, the present embodiment is not intended to be limited to these Examples.

Experimental Example 1

(Production of Organoid)

Adult stem cells were cultured by using media including FGF2 or a chimeric FGF at various concentrations in the presence or absence of EGF, and the formation of organoids was investigated.

<<Preparation of Medium>>

Regarding a basic medium, product name "Advanced DMEM/F12" (Thermo Fisher Scientific, Inc.) was used, and a medium to which the components described in the following Table 1 were added was prepared. In Table 1, "w/o EGF formulation" means a medium formulation that does not include EGF, and "w/EGF formulation" means a medium formulation that includes EGF.

Regarding a medium supplement, B-27 serum-free supplement (Thermo Fisher Scientific, Inc.) was used.

Regarding FGF2, product name "FGF-Basic, Human, Recombinant. Animal Free" (PeproTech, Inc.) was used. Furthermore, as a chimeric FGF, product name "FGFC" (FUJIFILM Wako Pure Chemical Corporation) was used.

Regarding EGF, product name "Animal-Free Recombinant Marine EGF" (PeproTech, Inc.) was used.

Regarding a Wnt signal promoter (Wnt signaling pathway promoter), mouse R-spondin 1 conditioned medium (self-prepared) and product name "Afamin/Wnt3a CM" (MBL Life Science Co., Ltd.) were used.

Regarding an insulin-like growth factor (IGF signaling pathway promoter), product name "Recombinant Human IGF-I/IGF-1 Protein, CF" (R&D Systems, Inc.) was used.

Regarding a TGF-β inhibitor (TGF-β signaling pathway inhibitor). A83-01 (TOCRIS Bioscience, Inc.) was used.

Regarding a ROCK inhibitor (ROCK signaling pathway inhibitor), product name "Y-27632, MF" (FUJIFILM Wako Pure Chemical Corporation) was used.

Regarding a BMP inhibitor (BMP signaling pathway inhibitor), mouse Noggin conditioned medium (self-prepared) was used.

TABLE 1

| Component | w/o EGF formulation | w/EGF formulation |
|---|---|---|
| Medium supplement | Final concentration 2% by volume | |
| FGF2 | Final concentration 2.5 to 10 ng/mL | Final concentration 3.1 to 50 ng/mL |
| FGFC | Final concentration 2.5 to 10 ng/mL | Final concentration 3.1 to 50 ng/mL |
| EGF | — | Final concentration 50 ng/mL |
| Wnt signal promoter (mouse R-spondin 1 conditioned medium) | R-spondin 1 final concentration 300 ng/mL | |
| Wnt signal promoter (Afamin/Wnt3a CM) | Wnt3a final concentration 400 ng/mL | |
| Insulin-like growth factor | Final concentration 1 μg/mL | |
| TGF-β inhibitor | Final concentration 500 nM | |
| ROCK inhibitor | Final concentration 10 μM | |
| BMP inhibitor | Noggin final concentration 100 ng/mL | |

<<Formation of Organoid>>

A large intestine tissue piece was used as a cell tissue piece including adult stem cells. More particularly, cells into which a reporter construct was introduced into the 18th exon of the LGR5 locus of cells derived from a large intestine tissue piece by genome editing were used in the experiment. LGR5 gene is a stem cell marker. Furthermore, IRES-tdTomato was used as a reporter construct. When this cell expresses LGR5, the cell expresses tdTomato, which is a fluorescent protein.

The above-described cells were embedded in 20 μL of Matrigel (registered trademark. Corning, Inc.) per 1000 cells and were seeded on a 48-well plate. Subsequently. Matrigel was left to stand at 37° C. to harden. Subsequently, a medium having each of the above-described compositions was added to the periphery of Matrigel. Thereafter, the medium was exchanged at an interval of every 2 to 3 days.

Subsequently, the expression of tdTomato was detected by observation with a fluorescence microscope, and the expression of LGR5 protein, which is a stem cell marker, was evaluated.

Figures 1A, 1B, 1C, 1D:
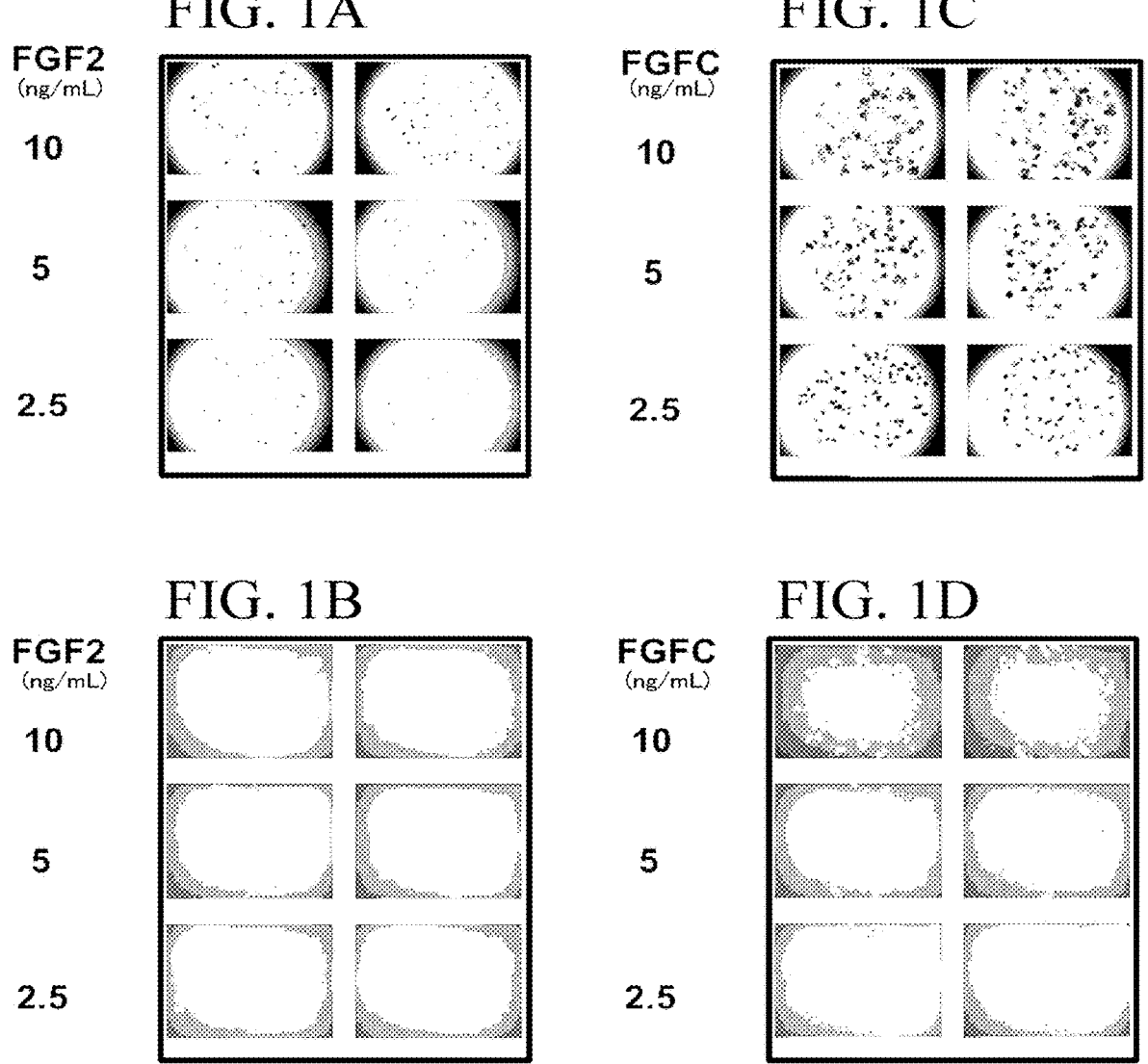
FIG. 1A is a micrograph of organoids formed in Experimental Example 1.
FIG. 1B is a micrograph of organoids formed in Experimental Example 1.
FIG. 1C is a micrograph of organoids formed in Experimental Example 1.
FIG. 1D is a micrograph of organoids formed in Experimental Example 1.

FIG. 1A to FIG. 1D are micrographs of organoids formed in the absence of EGF on the 9th day of culture. FIG. 1A is bright-field images of organoids formed in the presence of FGF2 at each of the concentrations shown in the figure. FIG. 1B is fluorescence micrographs showing that the expression of LGR5 protein was detected in the same field of view as in FIG. 1A. FIG. 1C is bright-field images of organoids formed in the presence of FGFC at each of the concentrations shown in the figure. FIG. 1D is fluorescence micrographs showing that the expression of LGR5 protein was detected in the same field of view as in FIG. 1C.

Figures 2A, 2B, 2C, 2D:
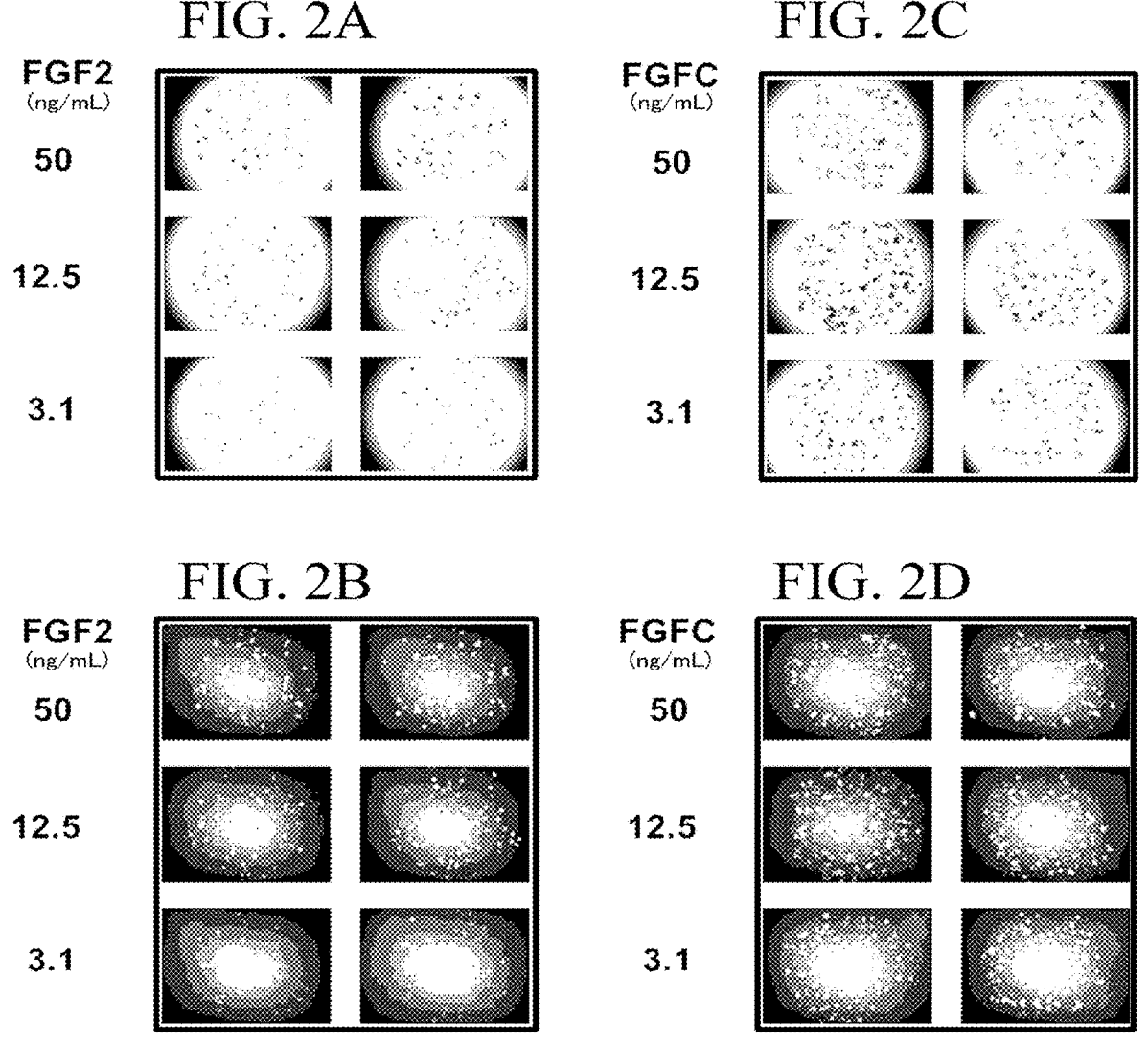
FIG. 2A is a micrograph of organoids formed in Experimental Example 1.
FIG. 2B is a micrograph of organoids formed in Experimental Example 1.
FIG. 2C is a micrograph of organoids formed in Experimental Example 1.
FIG. 2D is a micrograph of organoids formed in Experimental Example 1.

FIG. 2A to FIG. 2D are micrographs of organoids formed in the presence of EGF on the 8th day of culture. FIG. 2A is bright-field images of organoids formed in the presence of FGF2 at each of the concentrations shown in the figure. FIG. 2B is fluorescence micrographs showing that the expression of LGR5 protein was detected in the same field of view as in FIG. 2A. FIG. 2C is bright-field images of organoids formed in the presence of FGFC at each of the concentrations shown in the figure. FIG. 2D is fluorescence micrographs showing that the expression of LGR5 protein was detected in the same field of view as in FIG. 2C.

As a result, it was revealed that in the absence of EGF, the formation of organoids was insufficient even when adult stem cells were cultured in a medium including 10 ng/ml FGF2. On the other hand, it was revealed that organoids can be formed in a medium including FGFC, even in the absence of EGF. Furthermore, as shown in FIG. 1C and FIG. 1D, it was revealed that organoids can be formed even when the concentration of FGFC in the medium is reduced to about 2.5 ng/mL.

It was also revealed that organoids can be formed by culturing adult stem cells in a medium including 12.5 ng/mL FGF2 in the presence of EGF. It was revealed that in the presence of EGF, organoids can be formed even when concentration of FGFC in the medium is reduced to about 3.1 ng/mL.

Furthermore, it was revealed that the number of colonies formed was larger when a medium including FGFC was used, as compared with the case where a medium including FGF2 was used.

Experimental Example 2

(Production of FGFC Mutant)

Gene fragments encoding FGFC mutants were produced by artificial synthesis. The amino acid sequence of FGFC is set forth in SEQ ID NO:1. As the FGFC mutants, a mutant in which the 43rd glutamine residue of FGFC was substituted with valine (hereinafter, referred to as "FGFC-V", the amino acid sequence is set forth in SEQ ID NO:2), a mutant in which the 43rd glutamine residue of FGFC was substituted with isoleucine (hereinafter, referred to as "FGFC-1", the amino acid sequence is set forth in SEQ ID NO:3), and a mutant in which the 43rd glutamine residue of FGFC was substituted with leucine (hereinafter, referred to as "FGFC-L", the amino acid sequence is set forth in SEQ ID NO:4) were used.

Subsequently, the gene fragments encoding FGFC, FGFC-V, FGFC-I, and FGFC-L were each inserted into an expression vector pET-3a, expressed with BL21(DE3)pLysS to be purified as a protein, and the proteins were used in the following experiment.

Experimental Example 3

(Production of Organoids Using FGFC Mutants)

Adult stem cells were cultured by using media including FGFC or FGFC mutants at various concentrations, and the formation of organoids was investigated.

<<Preparation of Medium>>

Regarding a basic medium, product name "Advanced DMEM/F12" (Thermo Fisher Scientific, Inc.) was used, and a medium to which the components described in the following Table 2 were added was prepared. In Table 2, "w/o EGF formulation" means a medium formulation that does not include EGF, and "w/EGF formulation" means a medium formulation that includes EGF. Regarding FGFC and FGFC mutants, those prepared in Experimental Example 2 were used. Furthermore, regarding the EGF, Wnt signal promoter, insulin-like growth factor, TGF-β inhibitor, ROCK inhibitor, and BMP inhibitor, the same ones as those used in Experimental Example 1 were used.

TABLE 2

| Component | w/o EGF formulation | w/EGF formulation |
|---|---|---|
| Medium supplement | Final concentration 2% by volume | |
| FGFC or FGFC mutant | Final concentration 3.1 to 50 ng/mL | |
| EGF | — | Final concentration 50 ng/mL |
| Wnt signal promoter (mouse R-spondin 1 conditioned medium) | R-spondin 1 final concentration 300 ng/mL | |
| Wnt signal promoter (Afamin/Wnt3a CM) | Wnt3a final concentration 400 ng/mL | |
| Insulin like growth factor | Final concentration 1 μg/mL | |
| TGF-β inhibitor | Final concentration 500 nM | |
| ROCK inhibitor | Final concentration 10 μM | |
| BMP inhibitor | Noggin final concentration 100 ng/mL | |

<<Production of Organoid>>

Regarding a cell tissue piece including adult stem cells, cells similar to those used in Experimental Example 1 were used. First, cells were embedded in 20 μL of Matrigel (registered trademark. Corning, Inc.) per 1000 cells and were seeded on a 48-well plate. Subsequently, Matrigel was left to stand at 37° C. to harden. Subsequently, a medium having each of the above-described compositions was added to the periphery of Matrigel. Thereafter, the medium was exchanged at an interval of every 2 to 3 days.

Subsequently, the expression of tdTomato was detected by observation with a fluorescence microscope, and the expression of LGR5 protein, which is a stem cell marker, was evaluated.

Figures 3A, 3B, 3C, 3D:
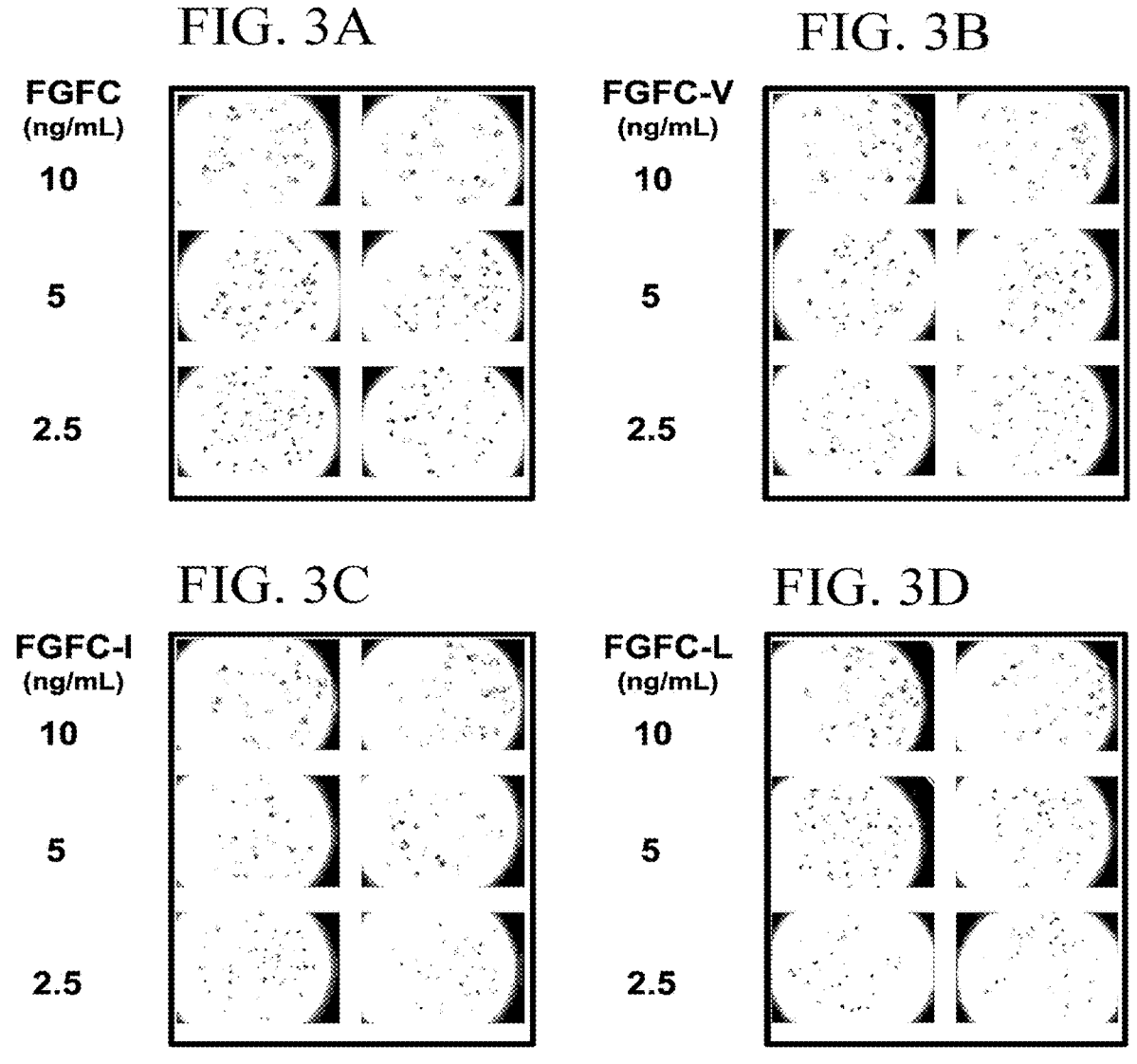
FIG. 3A is a micrograph of organoids formed in Experimental Example 3.
FIG. 3C is a micrograph of organoids formed in Experimental Example 3.
FIG. 3D is a micrograph of organoids formed in Experimental Example 3.

FIG. 3A to FIG. 3D are micrographs of each organoid on the 9th day of culture formed in the absence of EGF. FIG. 3A is bright-field images of organoids formed in the presence of FGFC at each of the concentrations shown in the figure. FIG. 3B is bright-field images of organoids formed in the presence of FGFC-V at each of the concentrations shown in the figure. FIG. 3C is bright-field images of organoids formed in the presence of FGFC-I at each of the concentrations shown in the figure. FIG. 3D is bright-field images of organoids formed in the presence of FGFC-L at each of the concentrations shown in the figure.

Figures 4A, 4B, 4C, 4D:
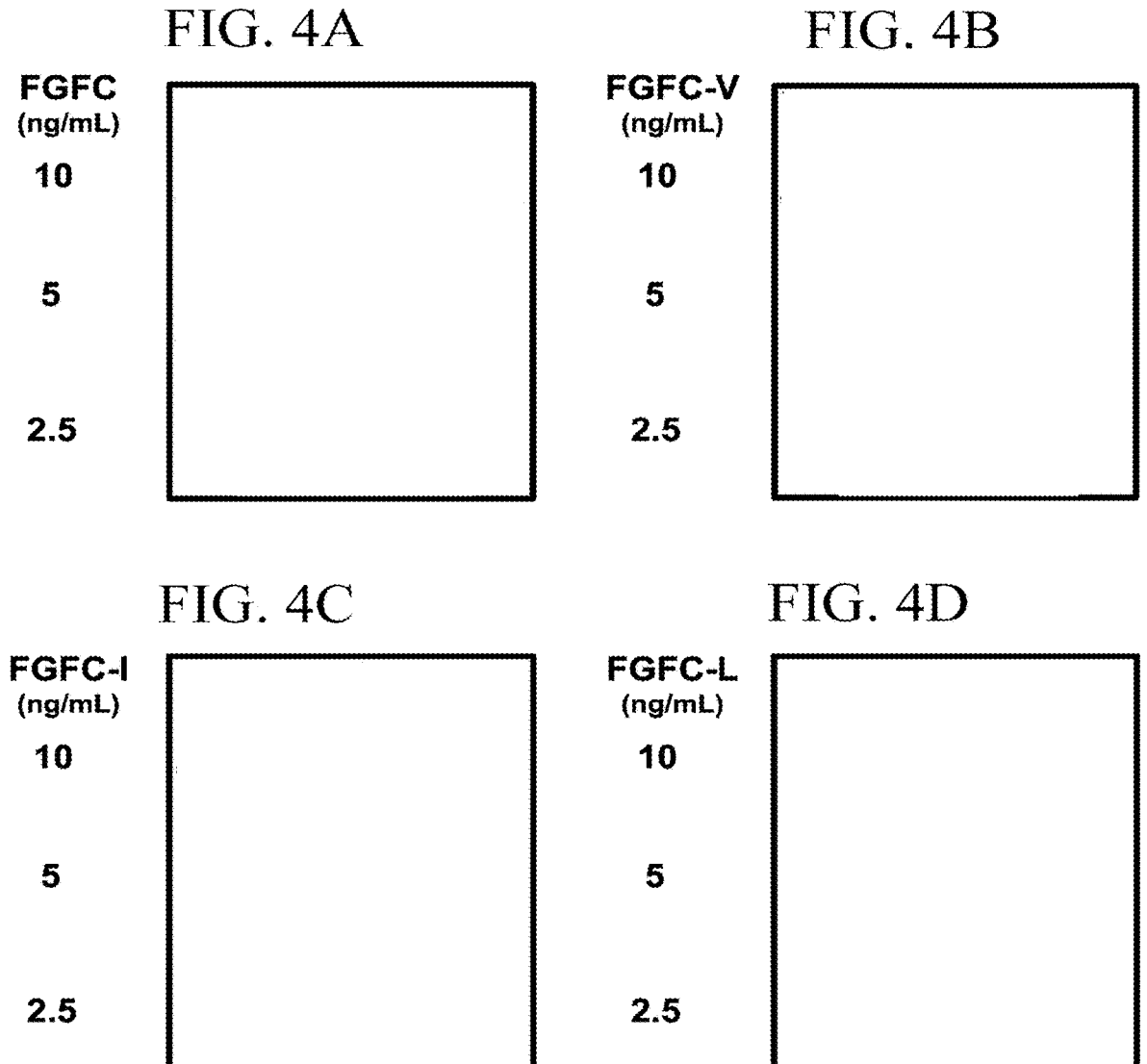
FIG. 4A is a micrograph of organoids formed in Experimental Example 3.
FIG. 4B is a micrograph of organoids formed in Experimental Example 3.
FIG. 4C is a micrograph of organoids formed in Experimental Example 3.
FIG. 4D is a micrograph of organoids formed in Experimental Example 3.

Furthermore, FIG. 4A is fluorescence micrographs showing that the expression of LGR5 protein was detected in the same field of view as in FIG. 3A. FIG. 4B is fluorescence micrographs showing that the expression of LGR5 protein was detected in the same field of view as in FIG. 3B. FIG. 4C is fluorescence micrographs showing that the expression of LGR5 protein was detected in the same field of view as in FIG. 3C. FIG. 4D is fluorescence micrographs showing that the expression of LGR5 protein was detected in the same field of view as in FIG. 3D.

Figures 5A, 5B, 5C, 5D:
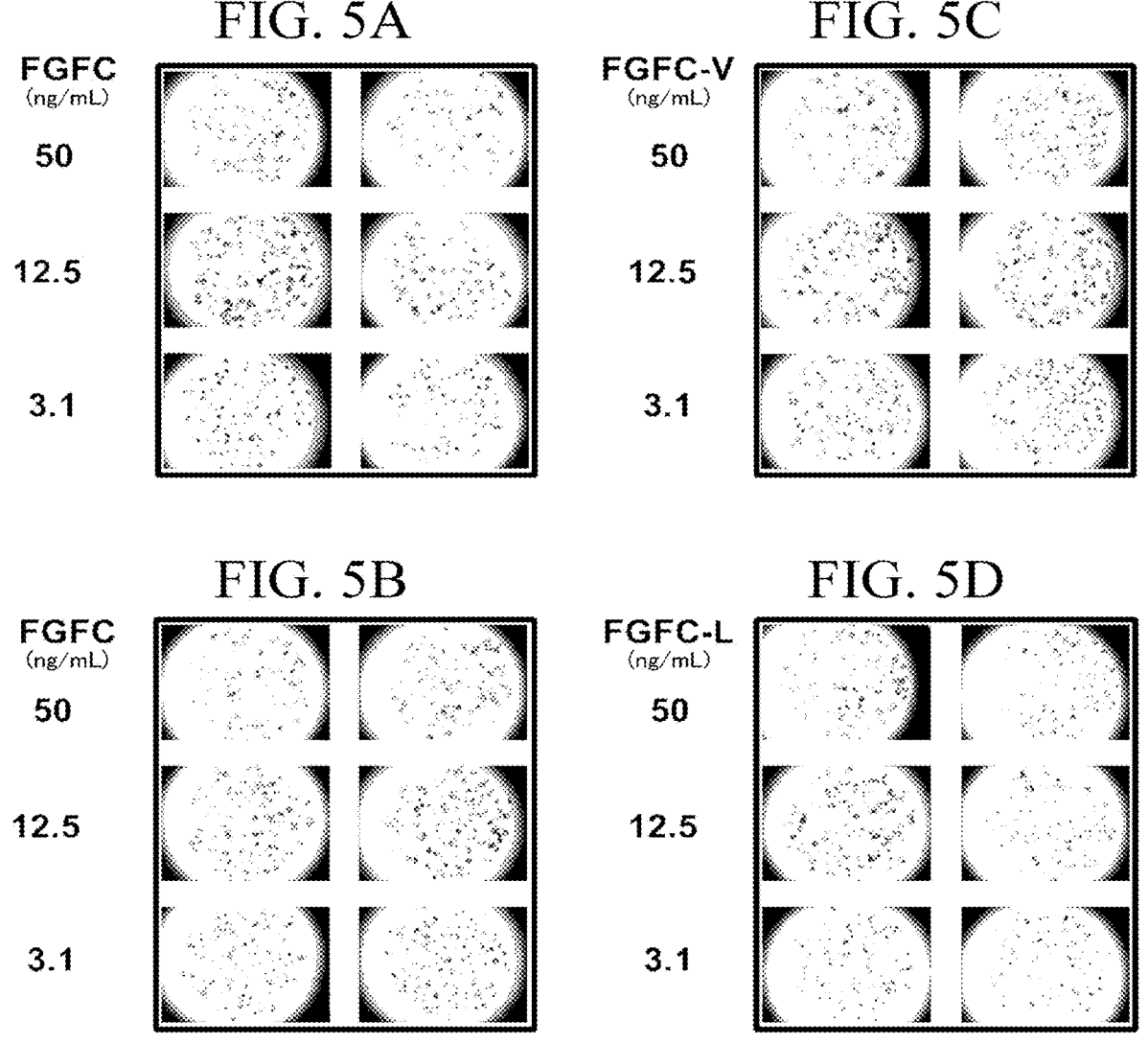
FIG. 5A is a micrograph of organoids formed in Experimental Example 3.
FIG. 5B is a micrograph of organoids formed in Experimental Example 3.
FIG. 5C is a micrograph of organoids formed in Experimental Example 3.
FIG. 5D is a micrograph of organoids formed in Experimental Example 3.

FIG. 5A to FIG. 5D are micrographs of each organoid on the 8th day of culture formed in the presence of EGF. FIG. 5A is bright-field images of organoids formed in the presence of FGFC at each of the concentrations shown in the figure. FIG. 5B is bright-field images of organoids formed in the presence of FGFC-V at each of the concentrations shown in the figure. FIG. 5C is bright-field images of organoids formed in the presence of FGFC-I at each of the concentrations shown in the figure. FIG. 5D is bright-field images of organoids formed in the presence of FGFC-L at each of the concentrations shown in the figure.

Furthermore, FIG. 6A is fluorescence micrographs showing that the expression of LGR5 protein was detected in the same field of view as in FIG. 5A. FIG. 6B is fluorescence micrographs showing that the expression of LGR5 protein was detected in the same field of view as in FIG. 5B. FIG. 6C is fluorescence micrographs showing that the expression of LGR5 protein was detected in the same field of view as in FIG. 5C. FIG. 6D is fluorescence micrographs showing that the expression of LGR5 protein was detected in the same field of view as in FIG. 5D.

As a result, it was revealed that regardless of which FGFC mutant was used, organoids can be produced to the same extent as the case where FGFC is used. Furthermore, as shown in FIG. 3A to FIG. 3D, FIG. 4A to FIG. 4D, FIG. 5A to FIG. 5D, and FIG. 6A to FIG. 6D, it was revealed that organoids can be produced even when the concentration of FGFC or the FGFC mutant in the medium is reduced to 2.5 ng/mL or 3.1 ng/mL.

Experimental Example 4

(Examination of Heat Resistance of FGFC Mutant)

The heat resistance of FGFC, FGFC-V, FGFC-I, and FGFC-L prepared in Experimental Example 2 was examined. Furthermore, for comparison, the heat resistance of FGF1 (product name "FGF-Acidic, Human, Recombinant", PeproTech, Inc.) and FGF2 (product name "FGF-Basic, Human, Recombinant, Animal Free", PeproTech, Inc.) was examined similarly.

To examine the heat resistance, a commercially available kit (product name "Protein Thermal Shift™ Dye Kit", Thermo Fisher Scientific, Inc.) was used, a sample was prepared according to the kit manual, and then the heat resistance of each protein was examined with a real-time PCR apparatus (product name "7500 fast", Thermo Fisher Scientific, Inc.). The measurement results were analyzed by using software (product name "Protein Thermal Shift™ Software v1.3", Thermo Fisher Scientific. Inc.).

FIG. 7 is a graph showing the measured melting temperature (Tm) of each protein. The axis of abscissa of the graph represents temperature (° C.). The Tm value of each protein is presented in the following Table 3.

TABLE 3

| Protein | Tm value (° C.) |
|---|---|
| FGF1 | 56.7 |
| FGF2 | 62.9 |
| FGFC | 64.4 |
| FGFC-V | 66.7 |
| FGFC-I | 68.3 |
| FGFC-L | 66.5 |

As a result, it was clarified that FGFC has higher heat resistance than FGF2. Furthermore, it was revealed that FGFC-V, FGFC-I, and FGFC-L have even higher heat resistance than FGFC.

INDUSTRIAL APPLICABILITY

According to the present embodiment, an organoid production technology capable of reducing the content of growth factors included in the medium can be provided.

The invention claimed is:

1. A production method for an organoid, the method comprising:

culturing adult stem cells or a stem cell tissue piece including adult stem cells in a medium comprising a chimeric Fibroblast Growth Factor (FGF) having the amino acid sequence of SEQ ID NO: 2, SEQ ID NO: 3, or SEQ ID NO: 4.

2. The production method according to claim 1, wherein a content of the chimeric FGF included in the medium is 50 ng/ml or less.

3. The production method according to claim 1, wherein the medium further comprises Epidermal Growth Factor (EGF).

4. The production method according to claim 3, wherein a total content of the chimeric FGF and the EGF included in the medium is 100 ng/ml or less.

5. The production method according to claim 1, wherein the medium further contains comprises an Insulin-like growth factor (IGF) signaling pathway promoter.

6. The production method according to claim 1, wherein the medium further comprises a Transforming Growth Factor-β (TGF-β) signaling pathway inhibitor.

7. The production method according to claim 1, wherein the medium further comprises a Wnt signaling pathway promoter.

8. The production method according to claim 1, wherein the medium further comprises a Rho-kinase (ROCK) signaling pathway inhibitor.

9. The production method according to claim 1, wherein the medium further comprises a Bone morphogenetic protein (BMP) signaling pathway inhibitor.

10. A medium comprising a chimeric FGF, wherein the chimeric FGF is a protein having the amino acid sequence of SEQ ID NO: 2, SEQ ID NO: 3, or SEQ ID NO: 4, and wherein a content of the chimeric FGF is 50 ng/ml or less.

11. The medium according to claim 10, wherein the medium further comprises EGF, and a total content of the chimeric FGF and the EGF is 100 ng/ml or less.

12. A chimeric FGF, wherein the chimeric FGF is a protein having the amino acid sequence of SEQ ID NO: 2, SEQ ID NO: 3, or SEQ ID NO: 4.

13. The production method according to claim 1, wherein the adult stem cells are epithelial stem cells.

* * * * *